United States Patent [19]

Ribeiro et al.

[11] Patent Number: 5,397,772

[45] Date of Patent: Mar. 14, 1995

[54] **VASODILATORY PEPTIDES FROM THE SALIVARY GLAND OF THE SAND FLY *LUTZOMYIA LONGIPALPIS***

[75] Inventors: Jose M. C. Ribeiro, Tuscon, Ariz.; Ethan A. Lerner; Heinz G. Remold, both of Brookline, Mass.; Richard G. Titus, Needham, Mass.

[73] Assignee: The President and Fellows of Harvard College, Cambridge, Mass.

[21] Appl. No.: 137,691

[22] Filed: Oct. 15, 1993

Related U.S. Application Data

[63] Continuation of Ser. No. 778,159, Jan. 5, 1992, abandoned, which is a continuation-in-part of Ser. No. 3374,080, Jun. 29, 1989, abandoned.

[51] Int. Cl.$^6$ ............... A61K 37/00; A61K 37/02; C07K 7/10; C12P 21/02
[52] U.S. Cl. .................... 514/12; 530/324; 530/334; 435/69.1; 930/DIG. 821
[58] Field of Search ............ 530/324, 334; 435/69.1; 930/821; 514/12

[56] References Cited

U.S. PATENT DOCUMENTS 4,839,343  6/1989  Waeber et al. ............... 514/12

OTHER PUBLICATIONS

Brain et al. "Calcitonin gene-related peptide is a potent vasodilator" Nature 1985, vol. 313, pp. 54–56.
Papst et al. J. Exp. Med. (1980) 151:101–114.
Amara et al. Nature (1982) 298:240–244.
Johnson et al. J. Immunol. (1983) 131(2):1038–1043.
Adams et al. Ann. Rev. Immunol. (1984) 2:283–318.
Pickett et al. Eur. J. Biochem. (1984) 143:35–38.
Murray et al. J. Immunol. (1985) 3:1619–1622.
Ribeiro et al. 83A Comp. Biochem. Physiol. (1986) 4:683–686.
Buus et al. Immunol. Reviews (1987) 98:115–141.
Unanue et al. Ann. L'Institute Pasteur (1987) 138:489–492.
Zaidi et al. Quart. J. Experimental Physiol. (19,87) 72:371–408.
Stryer et al. Biochem. (1988) Third Edition.
Titus et al. Science (1988) 239:1306–1308.
Tsunawaki et al. Nature (1988) 334:260–262.
Umeda et al. Biochem. Biophys. Research Comm. (1988) 154(1):227–235.
Casini et al. Naunyn-Schmiedeberg's Arch Pharmacol. (1989) 339:354–358.
Ribeiro et al. Science (1989) 243:212–214.

*Primary Examiner*—Douglas W. Robinson
*Assistant Examiner*—Jon P. Weber
*Attorney, Agent, or Firm*—Lahive & Cockfield

[57] ABSTRACT

Disclosed are proteins derived from the sand fly *Lutzomyia longipalpis* capable of inducing vasodilation in mammals, and data characterizing the proteins and nucleic acid encoding the proteins. Also disclosed is a method for temporarily inactivating the immune system in a mammal comprising administering to the mammal the Lutzomyia protein, CGRP, calcitonin, or active immune suppressing analogs thereof.

10 Claims, 6 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..189

( x i ) SEQUENCE DESCRIPTION: SEQ ID NO:1:

```
TGT GAT GCA ACA TGC CAA TTT CGC AAG GCC ATA GAT GAC TGC CAG AAG     48
Cys Asp Ala Thr Cys Gln Phe Arg Lys Ala Ile Asp Asp Cys Gln Lys
  1               5                  10                  15

CAG GCG CAT CAT AGC AAT GTT TTG CAG ACT TCT GTA CAA ACA ACT GCA     96
Gln Ala His His Ser Asn Val Leu Gln Thr Ser Val Gln Thr Thr Ala
             20                  25                  30

ACA TTC ACA TCA ATG GAT ACC TCC CAA CTA CCT GGA AAT AGT GTC TTC    144
Thr Phe Thr Ser Met Asp Thr Ser Gln Leu Pro Gly Asn Ser Val Phe
         35                  40                  45

AAA GAA TGT ATG AAG CAG AAG AAA AAG GAA TTT AAG GCA GGA AAG        189
Lys Glu Cys Met Lys Gln Lys Lys Lys Glu Phe Lys Ala Gly Lys
     50                  55                  60

TAAAATGATT GAAGAAAATT GTAGCCGAGG AGAGAAAGAA AGAAAGTCCC ATACCATATT  249

TTGTTTGTTA ATTGTAACGA ATTTTCCGAA AAATAAAT ATTATGCACT CAATTTAAAA   309

AAAAAA                                                            315
```

( 2 ) INFORMATION FOR SEQ ID NO:2:

( i ) SEQUENCE CHARACTERISTICS:
        ( A ) LENGTH: 63 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Cys Asp Ala Thr Cys Gln Phe Arg Lys Ala Ile Asp Asp Cys Gln Lys
  1               5                  10                  15

Gln Ala His His Ser Asn Val Leu Gln Thr Ser Val Gln Thr Thr Ala
             20                  25                  30

Thr Phe Thr Ser Met Asp Thr Ser Gln Leu Pro Gly Asn Ser Val Phe
         35                  40                  45

Lys Glu Cys Met Lys Gln Lys Lys Lys Glu Phe Lys Ala Gly Lys
     50                  55                  60
```

( 2 ) INFORMATION FOR SEQ ID NO:3:

(i) SEQUENCE CHARACTERISTICS:
  (A) LENGTH: 243 base pairs
  (B) TYPE: nucleic acid
  (C) STRANDEDNESS: single
  (D) TOPOLOGY: linear (ii) MOLECULE TYPE: genomic DNA (ix) FEATURE:
  (A) NAME/KEY: CDS
  (B) LOCATION: 1..240

(xi) SEQUENCE DESCRIPTION: SEQ ID NO:3:

| ATG | AAA | TAT | TCT | TTA | AAT | AAT | CTC | CAT | TTT | CTT | GTA | GAC | GTT | GCT | GAG | 48 |
| Met | Lys | Tyr | Ser | Leu | Asn | Asn | Leu | His | Phe | Leu | Val | Asp | Val | Ala | Glu | |
| 1 | | | | 5 | | | | 10 | | | | | 15 | | | |

| GGC | TGT | GAT | GCA | ACA | TGT | CAA | TTT | CGC | AAG | GCC | ATA | GAA | GAC | TGC | AGG | 96 |
| Gly | Cys | Asp | Ala | Thr | Cys | Gln | Phe | Arg | Lys | Ala | Ile | Glu | Asp | Cys | Arg | |
| | | | 20 | | | | | 25 | | | | | 30 | | | |

| AAG | AAG | GCG | CAT | CAT | AGC | GAT | GTT | TTG | CAG | ACT | TCT | GTA | CAA | ACA | ACT | 144 |
| Lys | Lys | Ala | His | His | Ser | Asp | Val | Leu | Gln | Thr | Ser | Val | Gln | Thr | Thr | |
| | | 35 | | | | | 40 | | | | | 45 | | | | |

| GCA | ACA | TTT | ACA | TCA | ATG | GAT | ACC | TCC | CAA | CTA | CCT | GGA | AGT | GGT | GTT | 192 |
| Ala | Thr | Phe | Thr | Ser | Met | Asp | Thr | Ser | Gln | Leu | Pro | Gly | Ser | Gly | Val | |
| | 50 | | | | | 55 | | | | | 60 | | | | | |

| TTC | AAA | GAA | TGC | ATG | AAG | GAG | AAA | GCT | AAG | GAA | TTT | AAG | GCA | GGA | AAG | 240 |
| Phe | Lys | Glu | Cys | Met | Lys | Glu | Lys | Ala | Lys | Glu | Phe | Lys | Ala | Gly | Lys | |
| 65 | | | | | 70 | | | | | 75 | | | | | 80 | |

TAG                                                                                                    243

(2) INFORMATION FOR SEQ ID NO:4:

(i) SEQUENCE CHARACTERISTICS:
    (A) LENGTH: 80 amino acids
    (B) TYPE: amino acid
    (D) TOPOLOGY: linear (ii) MOLECULE TYPE: protein (xi) SEQUENCE DESCRIPTION: SEQ ID NO:4:

| Met | Lys | Tyr | Ser | Leu | Asn | Asn | Leu | His | Phe | Leu | Val | Asp | Val | Ala | Glu |
| 1 | | | | 5 | | | | 10 | | | | | 15 | | |

| Gly | Cys | Asp | Ala | Thr | Cys | Gln | Phe | Arg | Lys | Ala | Ile | Glu | Asp | Cys | Arg |
| | | | 20 | | | | | 25 | | | | | 30 | | |

| Lys | Lys | Ala | His | His | Ser | Asp | Val | Leu | Gln | Thr | Ser | Val | Gln | Thr | Thr |
| | | 35 | | | | | 40 | | | | | 45 | | | |

| Ala | Thr | Phe | Thr | Ser | Met | Asp | Thr | Ser | Gln | Leu | Pro | Gly | Ser | Gly | Val |
| | 50 | | | | | 55 | | | | | 60 | | | | |

| Phe | Lys | Glu | Cys | Met | Lys | Glu | Lys | Ala | Lys | Glu | Phe | Lys | Ala | Gly | Lys |
| 65 | | | | | 70 | | | | | 75 | | | | | 80 |

(2) INFORMATION FOR SEQ ID NO:5:

(i) SEQUENCE CHARACTERISTICS:
    (A) LENGTH: 192 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..189

(ix) FEATURE:
    (A) NAME/KEY: misc_feature
    (B) LOCATION: 43-45

(D) OTHER INFORMATION: /label=NNN is AGG or CAG (ix) FEATURE:
    (A) NAME/KEY: misc_feature
    (B) LOCATION: 166-169
    (D) OTHER INFORMATION: /label=NNN is GCT or AAA (ix) FEATURE:
    (A) NAME/KEY: misc_feature
    (B) LOCATION: 12
    (D) OTHER INFORMATION: /label=Xaa is Glu or Asp (ix) FEATURE:
    (A) NAME/KEY: misc_feature
    (B) LOCATION: 15
    (D) OTHER INFORMATION: /label=Xaa is Arg or Gln (ix) FEATURE:
    (A) NAME/KEY: misc_feature
    (B) LOCATION: 17
    (D) OTHER INFORMATION: /label=Xaa is Lys or Gln (ix) FEATURE:
    (A) NAME/KEY: misc_feature
    (B) LOCATION: 22
    (D) OTHER INFORMATION: /label=Xaa is Asp or Asn (ix) FEATURE:
    (A) NAME/KEY: misc_feature
    (B) LOCATION: 45
    (D) OTHER INFORMATION: /label=Xaa is Ser or Asn (ix) FEATURE:
    (A) NAME/KEY: misc_feature
    (B) LOCATION: 46
    (D) OTHER INFORMATION: /label=Xaa is Gly or Ser (ix) FEATURE:
    (A) NAME/KEY: misc_feature
    (B) LOCATION: 54
    (D) OTHER INFORMATION: /label=Xaa is Glu or Gln (ix) FEATURE:
    (A) NAME/KEY: misc_feature
    (B) LOCATION: 56
    (D) OTHER INFORMATION: /label=Xaa is Ala or Lys (xi) SEQUENCE DESCRIPTION: SEQ ID NO:5:

```
TGT GAT GCA ACA TGY CAA TTT CGC AAG GCC ATA GAH GAC TGC NNN AAG          48
Cys Asp Ala Thr Cys Gln Phe Arg Lys Ala Ile Xaa Asp Cys Xaa Lys
 1               5                  10                  15

MAG GCG CAT CAT AGC RAT GTT TTG CAG ACT TCT GTA CAA ACA ACT GCA          96
Xaa Ala His His Ser Xaa Val Leu Gln Thr Ser Val Gln Thr Thr Ala
                 20                  25                  30

ACA TTY ACA TCA ATG GAT ACC TCC CAA CTA CCT GGA ART RGT GTY TTC         144
Thr Phe Thr Ser Met Asp Thr Ser Gln Leu Pro Gly Xaa Xaa Val Phe
             35                  40                  45

AAA GAA TGY ATG AAG SAG AAR NNN AAG GAA TTT AAG GCA GGA AAG             189
Lys Glu Cys Met Lys Xaa Lys Xaa Lys Glu Phe Lys Ala Gly Lys
 50                  55                  60

TAG                                                                     192
```

(2) INFORMATION FOR SEQ ID NO:6:

(i) SEQUENCE CHARACTERISTICS:
        (A) LENGTH: 63 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 12
        (D) OTHER INFORMATION: /label=Xaa is Glu or Asp -continued ( i x ) FEATURE:
        ( A ) NAME/KEY: misc_feature
        ( B ) LOCATION: 15
        ( D ) OTHER INFORMATION: /label=Xaa is Arg or Gln ( i x ) FEATURE:
        ( A ) NAME/KEY: misc_feature
        ( B ) LOCATION: 17
        ( D ) OTHER INFORMATION: /label=Xaa is Lys or Gln ( i x ) FEATURE:
        ( A ) NAME/KEY: misc_feature
        ( B ) LOCATION: 22
        ( D ) OTHER INFORMATION: /label=Xaa is Asp or Asn ( i x ) FEATURE:
        ( A ) NAME/KEY: misc_feature
        ( B ) LOCATION: 45
        ( D ) OTHER INFORMATION: /label=Xaa is Ser or Asn ( i x ) FEATURE:
        ( A ) NAME/KEY: misc_feature
        ( B ) LOCATION: 46
        ( D ) OTHER INFORMATION: /label=Xaa is Gly or Ser ( i x ) FEATURE:
        ( A ) NAME/KEY: misc_feature
        ( B ) LOCATION: 54
        ( D ) OTHER INFORMATION: /label=Xaa is Glu or Gln ( i x ) FEATURE:
        ( A ) NAME/KEY: misc_feature
        ( B ) LOCATION: 56
        ( D ) OTHER INFORMATION: /label=Xaa is Ala or Lys ( x i ) SEQUENCE DESCRIPTION: SEQ ID NO:6:

Cys Asp Ala Thr Cys Gln Phe Arg Lys Ala Ile Xaa Asp Cys Xaa Lys
 1               5                  10                      15

Xaa Ala His His Ser Xaa Val Leu Gln Thr Ser Val Gln Thr Thr Ala
        20                  25                      30

Thr Phe Thr Ser Met Asp Thr Ser Gln Leu Pro Gly Xaa Xaa Val Phe
            35                  40                  45

Lys Glu Cys Met Lys Xaa Lys Xaa Lys Glu Phe Lys Ala Gly Lys
        50                  55                  60

VASODILATORY PEPTIDES FROM THE SALIVARY GLAND OF THE SAND FLY *LUTZOMYIA LONGIPALPIS*

The United States government may have rights to this invention pursuant to NIH grant numbers AI24511, AI18694, and AI22794.

This application is a continuation application of U.S. Ser. No. 07/778,159, filed on Jan. 5, 1992, now abandoned, which is a continuation-in-part application of U.S. Ser. No. 07/374,080, filed Jun. 29, 1989, now abandoned.

BACKGROUND OF THE INVENTION

This invention relates to proteins capable of inducing vasodilation and temporary immune suppression in mammals, to compositions containing such proteins, to methods for producing the proteins using peptide synthesis and recombinant DNA techniques, and to synthetic forms of such proteins. The invention also relates to a method of desensitizing a mammal to the effects of an immunogen by administering certain peptides which temporarily inactivate the immune system.

Vasodilators are drugs useful in the treatment of various conditions characterized by constricted blood vessels. Such conditions include Raynaud's syndrome, certain post surgical complications of brain surgery involving sub arachnoid hemorrhage, heart failure, angina pactotis, and hypertension. Recently, the neuropeptide calcitonin gene-related peptide (CGRP) has been characterized as the most powerful and persistent vasodilator known. Calcitonin, another neuropeptide known primarily for its ability to prevent bone loss during periods of calcium stress, is derived from the same gene as CGRP. Despite weak structural homologies, there is enough similarity in the conformations of calcitonin and CGRP that they interact at each other's receptors. Thus, CGRP has a weak calcitonin-like effect on bone (Zaidi et al., *Ouart. J. Exp. Pasteur,* 72:371 (1987)).

The macrophage, a large phagocytic cell of the reticuloendothelial system, plays a central role in the induction and expression of cellular immunity. Antigen processing and subsequent presentation of antigen by macrophages in the presence of class II histocompatibility antigens can trigger helper T-lymphocyte response (Buss et al., *Immunol. Rev.* 98:115 (1987). In addition, macrophages can control T-cell responses via production of cytokines such as IL-1 (Unanue et al., *Ann, L'institute PaSteur* 138:489 (1987)).

Activation of macrophages enhances the microbicidal and tumoricidal activity of the cells, an event which is paralleled by significant changes in the levels of various intracellular, secreted and cell surface proteins (Adams et al., *Ann, Rev. Immunol.* 2:283 (1984)). For example, levels of secreted IL-1 and expressed class II histocompatability antigen rise, (Adams et al., ibid.) while the level of 5' nucleotidase has been shown to fall (Johnson et al., *J. Immunol.* 131:1038 (1983)). In addition, the production of $H_2O_2$ by activated macrophages is increased over controls (Adams et al., ibid.). Macrophages can be activated by a number of lymphokines such as IFN-$\gamma$ (Merry et al., *J. Immunol.* 134:1619 (1985)), and by bacterial cell wall products such as lipopolysaccharide (Pabst et al., *J. Exp. Med.* 151:101 (1980)). Recently, it has been suggested that as activated macrophages sterilize the site of inflammation they are deactivated so as to avoid possible damage to host tissue via continued release of cytotoxic products. (Tsunawaki et al., *Nature* 334:260 (1988)).

A first object of this invention is to provide proteins derived from the salivary lysate of the sand fly *Lutzomyia longipalpis* capable of vasodilation and of temporary immune suppression in mammals. Other objects are to characterize the protein, to provide natural and recombinant forms of the protein, and to provide genes encoding the protein and methods for production of the protein using recombinant DNA and peptide synthesis techniques. A second object is to provide methods for desensitizing a mammal to the effects of an immunogen by administering the protein derived from Lutzomyia, CGRP, calcitonin, active analogs, or synthetic forms thereof.

SUMMARY OF THE INVENTION

It has now been discovered that a protein derivable from the salivary gland lysate of the sand fly *Lutzomyia longipalpis* is capable of inducing vasodilation and/or temporary immune suppression in mammals. In one embodiment, the protein is characterized by a molecular weight of about 6800 daltons, and as eluting prior to CGRP in an acetonitrile-$H_2O$-trifluoroacetic acid-reverse phase-high performance liquid chromatography column. Its vasodilation activity is apparently at least 80 to 100 times as potent as CGRP, and like CGRP, persists for relatively long periods, e.g., several days.

Temporary immune suppression induced by this protein takes the form of inhibition of macrophage function as indicated by prevention of increase of $H_2O_2$ production by upon exposure to $\gamma$ IFN and by suppression of the macrophage's ability to present antigen to T-cells. It is believed that one active protein is responsible for both the vasodilation and immune suppression activities.

The protein ("Lutzomyia Protein" or "LP") can be derived from lysate of the salivary glands of the sand fly by chromatographic purification as disclosed herein. The nucleotide sequence of a gene encoding LP has been determined and the amino acid sequence deduced. A second DNA sequence encoding LP has also been identified which varies somewhat from the first sequence determined both in terms of nucleotide sequence and the deduced amino acid sequence. It appears, therefore, that there are two or more variants of LP. The protein and various active analogs and fragments thereof can be produced by expression of recombinant DNA in a host cell or by peptide synthesis techniques. Compositions rich in LP or its active analogs and fragments may be used pharmaceutically as an immune system suppressing drug or as a potent vasodilator. The active analogs and fragments of LP are typically proteins or peptides comprising an amino acid sequence sufficiently duplicative of the sequence of the active portion of an LP protein such that the proteins or peptides are capable of inducing vasodilation or temporary immune suppression in a mammal.

Thus, in another aspect, the invention comprises a method of increasing blood flow in the circulatory system of a mammal by administering to the mammal an effective amount of LP, or active analog or fragment thereof, to cause vasodilation in the mammal. Parenteral administration can result in systemic vasodilation activity. Topical application, e.g., to a vascular bed during surgery, can serve to concentrate the vasodilatory effect in the locus of application.

In another aspect, it has been discovered that, in addition to LP, the structurally related CGRP and calcitonin peptides also can be used to suppress the immune system temporarily. The invention thus further provides a method of desensitizing a mammal to the effects of an immunogen by parenterally administering LP, calcitonin, CGRP, active analogs or fragments thereof, or mixtures thereof in amounts effective to temporarily inactivate the immune system. Thus, for example, these temporary immune suppressing substances may be administered in conjunction with a protein xenotypic to the mammal (such as streptokinase or a murine monoclonal in man) so as to inhibit or prevent the development of antibodies or cellular immunity to the protein. The immune suppressing substances may also be used to treat graft rejection and autoimmune disease.

BRIEF DESCRIPTION OF THE DRAWING

The foregoing and other objects and features of the invention, as well as the invention itself, may be more fully understood from the following description, read together with the accompanying drawings, in which.

DESCRIPTION

Figure 1:
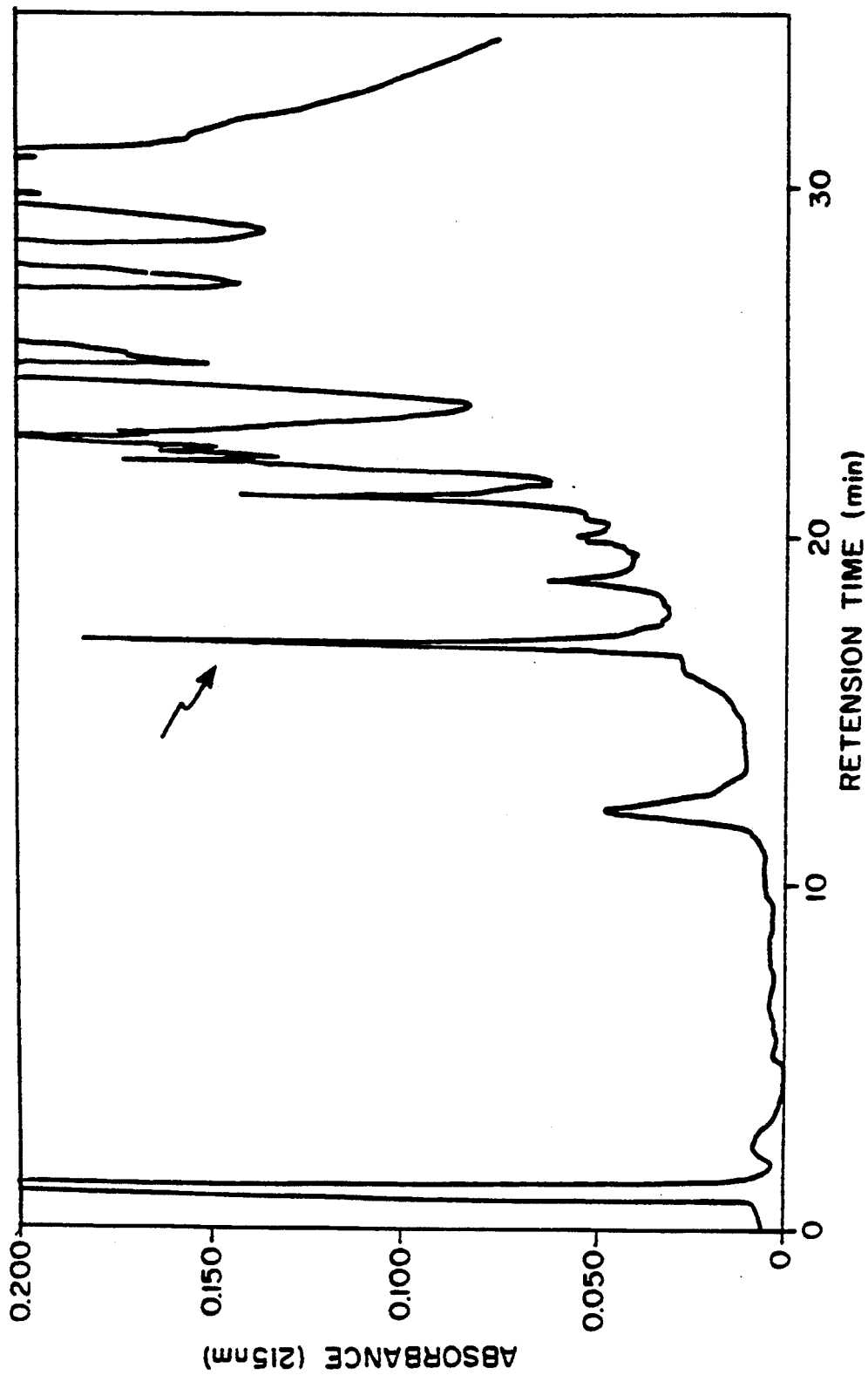
FIG. 1 shows a reverse-phase HPLC chromatogram of salivary gland extract.

An active protein (LP) in the saliva lysate of the sand fly *Lutzomyia longipalpis* has been discovered to be a potent vasodilator. In addition, it has been discovered that calcitonin, CGRP and LP all exhibit an ability to suppress temporarily the immune system of mammals.

LP can be obtained by conventional purification chromatography from surgically excised salivary glands of *L. longipalpis* as disclosed below. One pair of salivary glands contains 10–15 ng LP.

The nucleotide sequence which codes for LP (SEQ. ID. No: 1) and the amino acid sequence of LP (SEQ. ID. No: 2) are given in the sequence listing at page 29. Knowledge of the LP sequence enables skilled engineers to produce large quantities of the protein for therapeutic use. The artisan can synthesize LP or active analogs thereof using conventional chemical solid or solution phase peptide synthesis techniques. In addition, knowledge of the sequence permits a DNA sequence coding for LP or active analogs or fragments thereof in various types of host cells, including both procaryotes and eucaryotes, to produce large quantities of the protein, or active analogs or fragments thereof, and other constructs capable of inducing vasodilation or temporary immune suppression in a mammal.

The compounds of the present invention can be formulated into pharmaceutical preparations for therapeutic use. In particular, LP can find use as a therapeutic vasodilating agent and consequently as a regulator of blood pressure. Also, CGRP and calcitonin (both available commercially) as well as LP may be used to induce temporary immune suppression.

These compounds can be administered to mammalian hosts for veterinary use such as with domestic animals, and for clinical use in humans in a manner similar to other therapeutic agents. In general, the dosage will range from about 2 pg to 0.25 $\mu$g per kg of host body weight. Dosages within these ranges can be used in an amount per administration which may vary depending on the severity of the condition treated until benefits have been obtained. The protein can be injected intravascularly to provide a systemic vasodilation effect to treat, for example, Raynaud's syndrome. It also may be applied topically or by infusion to induce locally a vasodilatory action, for example, during brain surgery to alleviate blood vessel constriction and subsequent brain damage. These compounds may be formulated for oral, buccal, parenteral, or rectal administration or in a form suitable for nasal administration or administration by inhalation or insufflation.

These compounds can be administered neat, as mixtures with other pharmacologically active or inactive materials, or with physiologically suitable carriers such as, for example, water, normal saline, or buffers compatible with physiological conditions. Injection can be subcutaneous, intravenous, or intramuscular. These compounds may be administered as pharmacologically acceptable salts such as acid addition salts. The protein may be stored in lyophilized form and reconstituted just prior to use.

The subject matter claimed herein will be further understood from the following.

Isolation of LP

Sand flies were reared from a laboratory strain of *Lutzomyia longipalpis* originally provided by the Walter Reed Army Institute of Research following the procedure described by Modi et al., *J. Med. Entomol.* 20:568–570 (1983). Wild specimens can be captured in various tropical regions in South America. Larvae were fed a mixture of fermented rabbit feed (Purina), rabbit faeces, and liver powder. Adults were kept at 100% relative humidity and were given free access to a saturated sucrose solution. Salivary glands are dissected from 5–7 day old female flies and stored in phosphate-buffered saline containing 1 mg/ml bovine serum albumin (PBS-BSA). The glands are excised using a #5 forceps and surgical needles to remove the prominent glands posterior to the head. Pairs of glands are transferred to 20 $\mu$l of Tris-HCl buffer, 5 mM, pH 7.4, and may be frozen at $-70°$ C. until needed.

Characterization of LP

Reversed-phase high-performance liquid chromatography (HPLC) on the extract of 105 pairs of salivary glands is depicted in FIG. 1. 105 pairs of salivary glands were dissected in PBS. Lysates were made by freeze-thawing. The extract was spun in a microcentrifuge for 30 seconds before being applied to the column. A C-18 micropellicular HPLC column (Glycotech) was equilibrated with 20% acetonitrile/0.1% trifluoroacetic acid at 50° C. at a flow rate of 0.6 ml/minute. Three minutes after injection, a linear gradient was run for 20 minutes reaching 44% acetonitrile. Fractions were collected every 30 seconds and assayed for vasodilator activity. The vasodilator assay was performed by diluting material from the gradient 10 fold and injecting 50 μl intradermally into the shaved back of a rabbit. The development of erythema at the injection site corresponded with the peak indicated. One μg of human CGRP, used as a control peptide, eluted as a peak of equal area, five minutes later (not shown). This observation implies that approximately ten nanograms of LP are present per pair of salivary glands.

Figure 2:
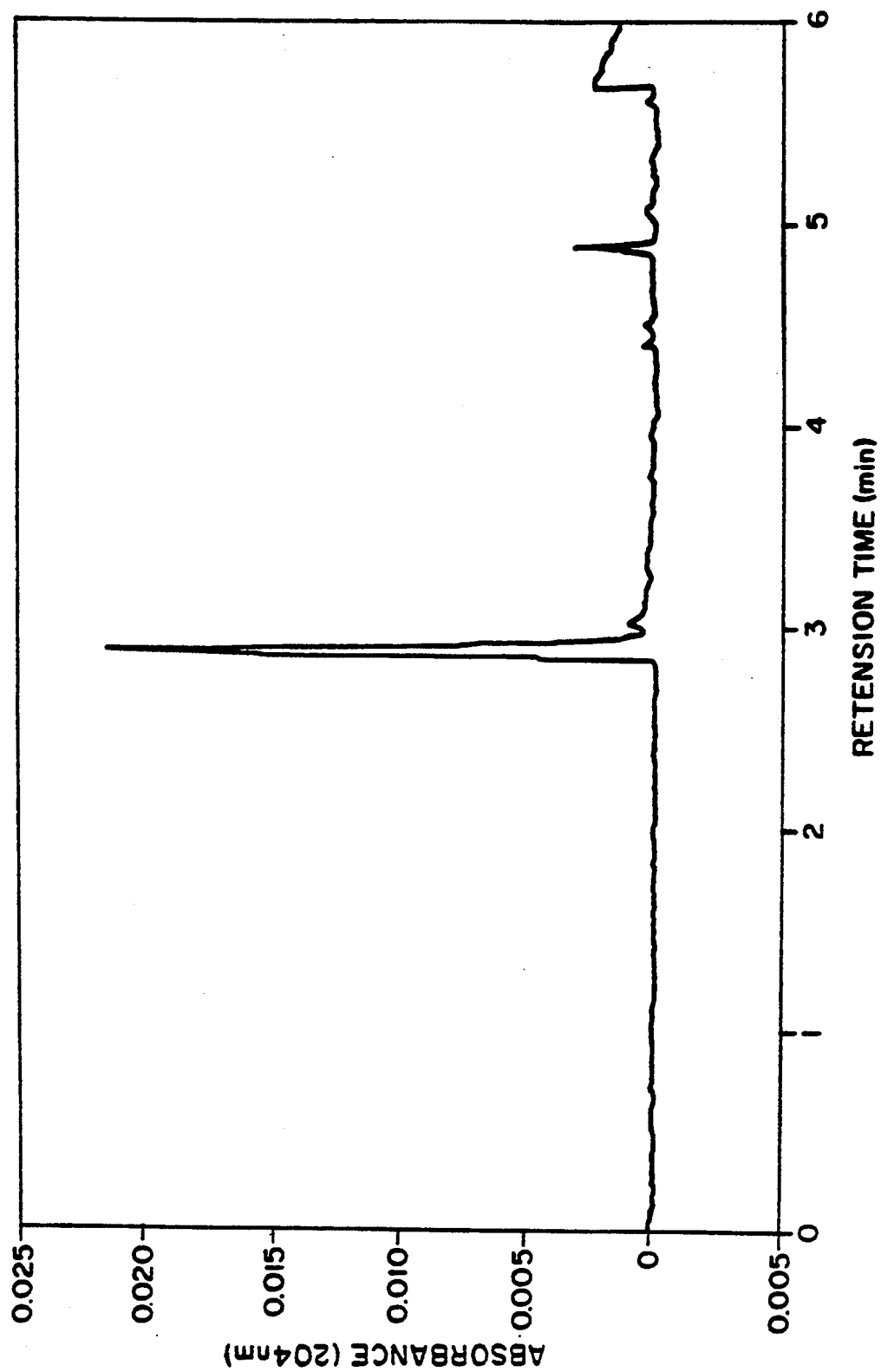
FIG. 2 shows the results of capillary electrophoresis of reverse-phase HPLC purified LP.

Because multiple components could be hidden under a single peak from HPLC, an independent measure of LP purity was needed. Capillary electrophoresis, which can separate molecules on the basis of charge, was chosen. The limitation here was the need to have a volume of a few microliters where the concentration of LP would approximate the 1 mg/ml used in capillary electrophoresis. 250 pairs of salivary glands were dissected and 2.5 μg of LP isolated from multiple runs on RP-HPLC. The fractions containing LP were pooled, yielding a volume of approximately two ml. LP was concentrated in a Speed-Vac to a volume of 10 μl in preparation for capillary electrophoresis. Sample was injected for three seconds at ½ psi and electrophoresed at 25 kv on a Beckman P/ACE 2000 instrument. A 100 mM borate buffer of pH 8.3 was chosen because isoelectic focusing of the HPLC-purified EIP revealed activity at a pI of 7.8. The sloping peak near six minutes represents trifluoroacetic acid remaining from the HPLC run. A large peak was present after nearly three minutes of electrophoresis (FIG. 2).

0.5 microgram of RP-HPLC purified LP was analyzed via fast-atom-bombardment (FAB) mass spectrometry in order to determine its mass. A single component of 6839 mass units was detected. The mass of LP is thus different from that of 3900 for CGRP.

Figure 3:
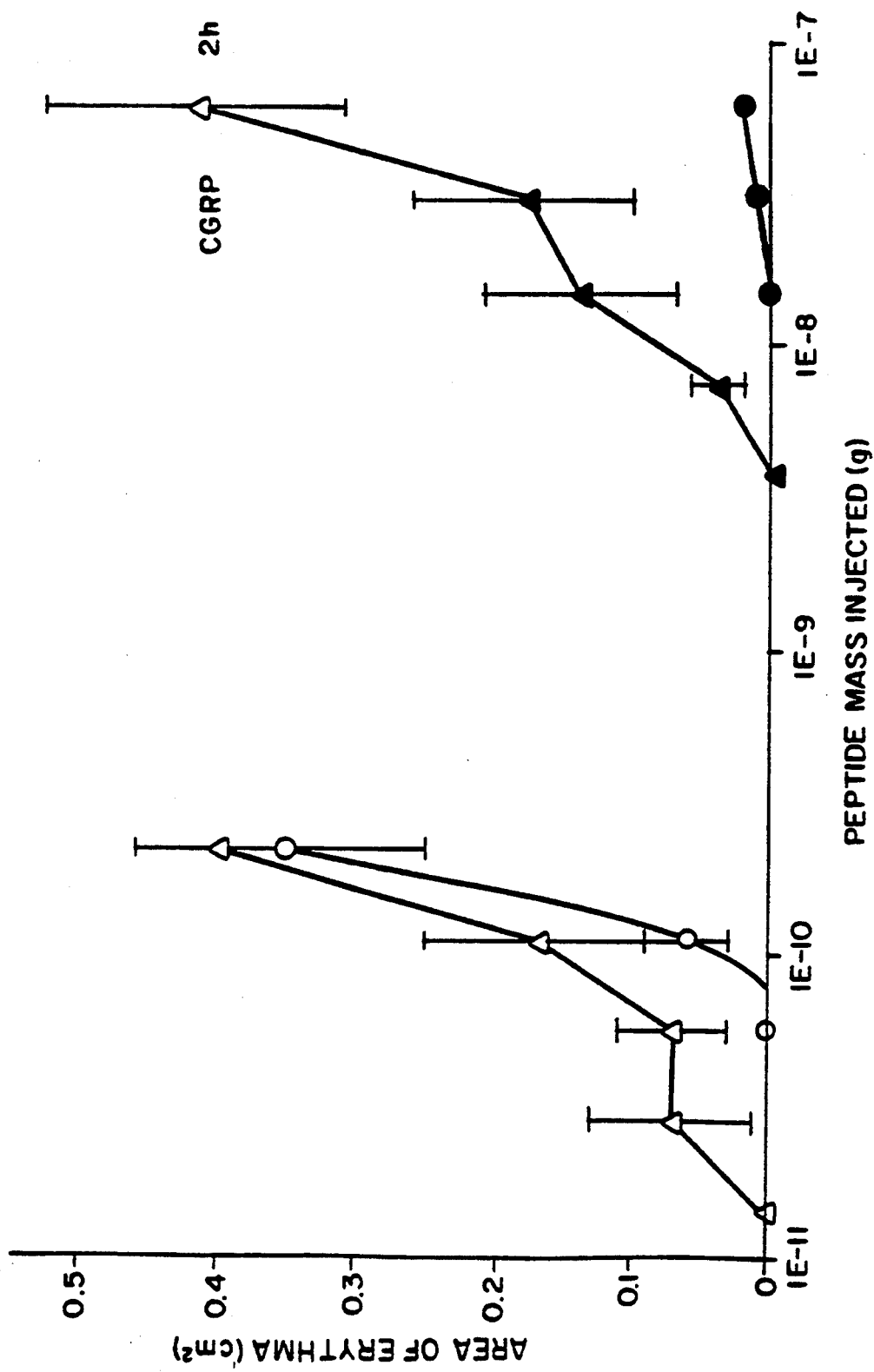
FIG. 3 is a graph showing the potency and persistence of erythema induced by LP and CGRP.

The vasodilatory activity of RP-HPLC purified LP as compared to synthetic human α-CGRP on rabbit skin is shown in FIG. 3. The amount of LP injected into the skin was based on the area of the absorbing peak collected from RP-HPLC. The indicated amounts of RP-purified LP or synthetic CGRP, in a volume of 50 μl of PBS, were injected into the shaved back of a rabbit. The area of resultant erythema was measured at 2 hours (triangles) and again at 4 hours (circles). Bars represent average and SE of triplicate injections. Two hours after injection, 0.1 nanograms of LP gives an erythema equivalent to 50 nanograms of CGRP. At 4 hours, erythema from LP is still present whereas the CGRP injection site has only residual erythema.

Demonstration of Vasodilatory Activity of LP

Figure 4:
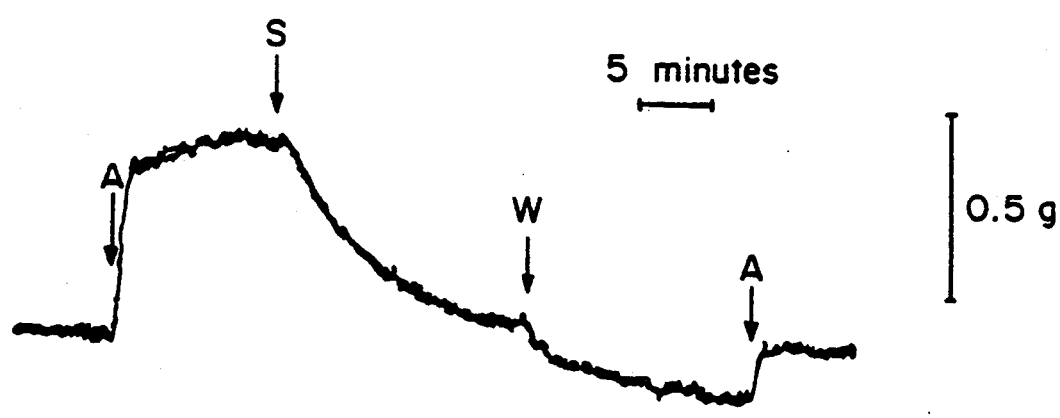
FIG. 4 is a graph representing the level of relaxation of a constricted rabbit aortic ring by *Lutzomyia longipalpis* salivary gland lysate measuring tension vs. time; A indicates addition of the vasoconstrictor adrenalin; S indicates addition of salivary gland lysates; W represents washing of the preparation; the second A represents a second addition of adrenalin.

The vasodilatory activity of the LP is shown by the relaxation of a constricted rabbit aortic ring by *Lutzomyia longipalpis* salivary gland lysates. In FIG. 4, A indicates the addition of adrenaline, 200 mg total; S represents the addition of the salivary gland lysate from three sand flies (approx. 30–40 ng LP); and W represents the washing of the preparation. Thoracic aortas were obtained from adult New Zealand rabbits. 4 mm-wide rings were suspended on a 3-ml bath containing Tyrode's solution bubbled with 95% $O_2$ and 5% $CO_2$ and kept at 37° C. under initial tension of 1 g (Webster et al., *Meth. Enzymol.* 293:531–541 (1970)).

An auxotonic pendulum level (Paton, *J. Physiol. Lond.* 137:35P–36P (1957) coupled to a Harvard isotonic transducer served to measure the contractions. In four experiments, relaxation of more than 50% was achieved when homogenate from 3 pairs of glands were added to the 2.5 ml chamber (58±8%, mean±S.E.) In all cases there was a 15–30 second delay between addition of the salivary homogenate and beginning of the relaxation. After the preparation was washed, further addition of adrenaline did not restore the pre-treatment level of contraction, indicating that the activity persisted (FIG. 4). The duration of the erythema induced by LP upon injection into mammalian skin suggests the vasodilation activity lasts at least 24 hours.

Amino Acid Sequence Determination

HPLC-purified biologically active LP was subjected to amino acid micro-sequencing. Amino acid residues 3–13 were determined but not residues 1 or 2 of the mature protein sequence. A degenerate oligonucleotide was used in conjunction with an oligo-dT primer in the polymerase chain reaction to directly amplify a miniscule amount of LP cDNA which had been made from about 60 cells, or 1/5th of a pair of salivary glands. This amplified DNA sequence was missing the most 5' end coding for amino acids 1 and 2 and upstream sequences including the signal sequence and promoter. However, this DNA sequence yielded the nucleotide sequence 3' to the nucleotides coding for amino acid residue 14. This sequence information was used to select a genomic clone from a sand fly genomic library. A new oligonucleotide was then prepared from the genomic DNA which had the sequence from the signal peptide, along with an oligonucleotide from the 3' untranslated region of the LP cDNA. These oligonucleotides were used as primers to amplify the cDNA coding for the complete sequence, including residues 1 and 2, which was then sequenced by standard technique. The nucleotide sequence of the cDNA and the deduced amino acid sequence of the mature LP are shown as SEQ ID NO: 1 and 2, respectively in the sequence listing at page 29. The genomic LP DNA sequence, shown as sequence 7 in the sequence listing at page 30, varies somewhat from the LP cDNA sequence and is believed to represent a variant LP gene and includes the DNA sequence and deduced amino acid sequence of the 17 amino acid leader peptide (SEQ ID NO: 4). The signal sequence of LP is also given in sequence 3 (nucleotides 1–51).

Solid Phase Peptide Synthesis

The LP peptide may be prepared conveniently using standard solid-phase peptide synthesis (Merrifield, *Proc. Fed. Amer. Soc. Exp, Biol,* 24:412 (1962)). In such a synthesis, the solid phase support acts as a C-terminal protecting group for the growing oligomer chain. Thus, in general, N-terminal protected amino acid or peptide is reacted with a suitably functionalized and soluble polymer such that the C-terminal residue is attached to the insoluble support. The N-terminal protecting group is then selectively removed from the aminoacyl polymer and the next N-protected amino acid or peptide is coupled to the polymer using a suitable reagent for reaction of the carboxyl group of the amino acid or peptide to be introduced. The cycle of deprotection and coupling can be repeated as necessary, using the appropriate amino acid or peptide derivatives, to assemble on the polymer carrier the desired amino acid sequence of the peptide. Once the sequence is complete, a more rigorous reagent is applied to the peptide/polymer, to cleave the bond linking the peptide to the polymer, thus liberating the peptide which can be recovered using conventional techniques. Depending on the conditions used, the peptide may have a C-terminal acid or amide group and may, or may not, possess a N-terminal protecting group.

It will also be appreciated that any other reactive group(s) such as amino, carboxy, hydroxy, or mercapto group(s) if present, will have been suitably protected during the synthesis and may still be in a protected state after cleavage of the peptide from the polymer. Further processing of the peptide is therefore often necessary to obtain the desired compound.

Peptide synthesis including the introduction and removal of protective groups is well known in the art. See for example "The Peptides" Volume 3, Gross and Meienhoffer, Academic Press, 1981. The amino acid or peptide starting materials, or reactive derivatives thereof for use in the solid phase synthesis, are either known compounds, or may be prepared by methods analogous to those used for the preparation of the known compounds. Particular reagents which may be used for activation of the carboxyl group of the amino acid or peptide include for example imides such as dicyclohexylcarbodiimide.

The resin may be, for example, an insoluble polymeric support, e.g. a polyamide resin such as a cross-linked polydimethylacrylamide resin or any inert macroreticular resin such as polystyrene cross-linked with divinyl benzene or a methyl benzhydrylamine resin.

Two procedures have been found which are useful in the preparation of compounds of the invention. The first of these is the BOC procedure, where the protectant group used in the synthetic cycle is a tertiary butoxycarbonyl group. The BOC protectant group is selectively removed at each stage using trifluoroacetic acid and dichloromethane. After completion of the synthetic cycles the peptide is removed from the resin by treatment with hydrogen fluoride and anisole. The second procedure is known as the FMOC procedure and utilizes a fluorenylmethoxycarbonyl group which is selectively removed using 20% piperidine in dimethylformamide. The peptide is cleaved from the resin by treatment with trifluoroacetic acid and anisole.

Calcitonin and CGRP have a C-terminal amide group which is necessary for activity. If LP requires amidation, it may be provided by appropriate choice of the cleavage conditions used in the solid phase synthesis described above. Thus, the compound may be cleaved from the support and amidated in a one-step process by treatment with, for example, methanol and ammonia. Alternatively, where the cleavage conditions are chosen to yield a peptide with a C-terminal carboxylic acid, the amide, if necessary, may be obtained by conventional means, for example where the penultimate C-terminal residue is leucine, by enzymatic treatment with carboxypeptidase Y, and where the penultimate residue is glycine, with amidating enzyme (Bradbury, et. al., Nature 298:240–244 (1982)), or by chemical treatment of the peptide with, for example, ammonia. Alternatively solution phase peptide synthesis techniques may be used for preparation of the LP peptide.

Recombinant Production of LP

Knowledge of the amino acid sequence of LP also permits production of the protein using recombinant DNA techniques which are well known. Thus, a gene encoding the amino acid sequence, or various analogs thereof, can be produced, for example, by oligonucleotide synthesis and subsequent ligation if necessary to form a complete coding region. The coding region may be ligated to 3' and 5' untranslated DNA regions constituting, as required, a poly A site, promoter, ribosome binding site, stop and start codons, etc. Fused DNAs, e.g., comprising DNA coding for a host polypeptide and LP polypeptide can be used for production of fusion proteins comprising LP polypeptides. The construction of an expression vector suitable for production of LP products in a selected cell type also is within the skill of the art. Culture of transformed cells results in intracellular accumulation or secretion of protein which may be purified, refolded, and otherwise post translationally modified as desired or as necessary.

Temporary Immune Suppression

Assay of $H_2O_2$ Production by Macrophages as a Marker of Immune Stimulation

Monocytes obtained by leukophoresis of healthy volunteers were purified on Ficoll-hypaque and Percoll (Pharmacia, Piscataway, N.J.) gradients and placed into microliter wells ($5 \times 10^5$/well) in RPMI-1640 (GIBCO, Grand Island, N.Y.) with 5% pooled normal human serum and 1% gentamycin (M.A. Bioproducts, Walkinville, Md.). The cells were greater than 95% macrophages as judged by esterase staining. (The Manual of Macrophage Methodology, Herscowitz et al., eds. Marcel Dekker, N.Y., p. 199 (1981)). After one day in culture, non-adherent cells were rinsed away and the macrophages were treated, e.g., with human CGRP, Calcitonin, or LP as described below. Following treatment, the macrophages were incubated for three days with a concentration of from 100 to 400 units interferon gamma (Amgen Biologicals, Thousand Oaks, Calif.), in medium with 15% pooled normal human serum, at which time the $H_2O_2$ concentration in the cells was determined.

$H_2O_2$ production by macrophages was determined by fluorometric assay using the fluorophore scopoletin (de la Harpe et al., J. Immunol. Methods 78:323 (1985)). Wells containing macrophages were washed and incubated for 90 minutes with a buffered solution of scopoletin (Sigma, St. Louis, Mo.), PMA (Sigma, St. Louis, Mo.), and horseradish peroxidase (HRPO) (Sigma, St. Louis, Mo.). Triggered by PMA, an activated macrophage releases $H_2O_2$ which oxidizes scopoletin to a non-fluorescent product in a reaction catalyzed by HRPO. The amount of $H_2O_2$ released per culture is determined as nanomoles $H_2O_2$. To control for variations in cell numbers from culture to culture, the data were normalized to $\mu$g of DNA per culture; all data are presented as nanomoles $H_2O_2$ released/$\mu$g DNA/hour. DNA was determined by a fluorescence assay (Kissane et al., J. Biol. Chem. 233:184 (1958).

CGRP Inhibition of Macrophage Function

Figure 5:
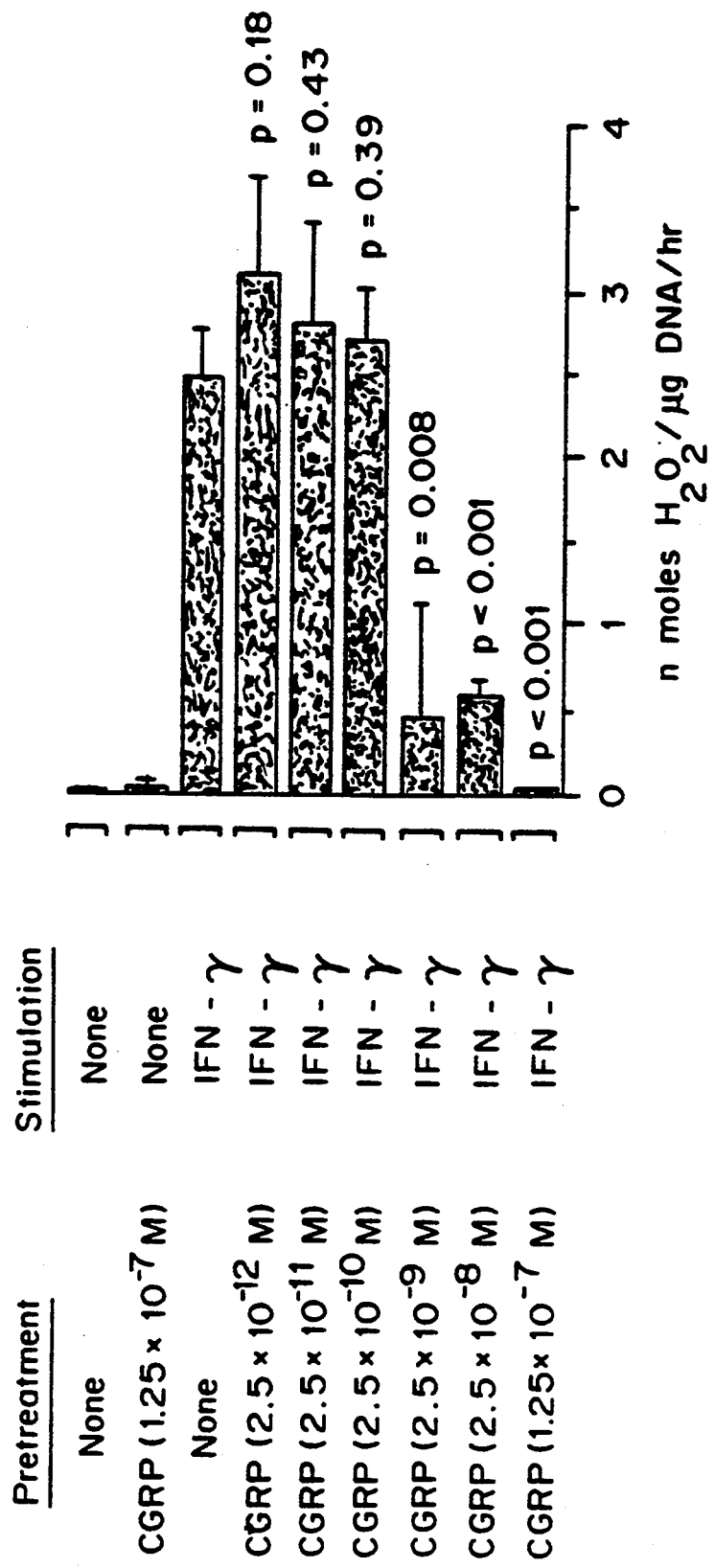
FIG. 5 is a bar graph showing the effect of CGRP on $H_2O_2$ production of human macrophages pretreated with Interferon-$\gamma$; the bars represent mean $H_2O_2$ production for triplicate cultures±standard deviation (SD)

Human macrophage monolayers were pretreated for three hrs. with varying concentrations of human CGRP. The cells were activated with IFN-$\gamma$ (100 to 400 units/per ml.) for 72 hrs. The amount of $H_2O_2$ produced by the cells was then determined according to the above procedure. The bars in FIG. 5 represent mean $H_2O_2$ production for triplicate cultures$\pm$SD. The p values were derived by comparing the mean $H_2O_2$ response obtained in each of the CGRP-treated groups with the $H_2O_2$ response obtained in the positive control cultures not treated with CGRP but stimulated with IFN-γ. Similar results were obtained in 4 replicate experiments. CGRP was found to markedly inhibit the ability of the macrophages to produce $H_2O_2$ in response to IFN-γ (FIG. 5). Concentrations of CGRP as low as $2.5 \times 10^{-9}$ M significantly inhibited $H_2O_2$ production by the macrophages; higher concentrations completely abrogated the production of $H_2O_2$ (FIG. 5). Results given in FIG. 5 utilize 200 units/ml of IFN-γ, the optimal concentration to stimulate the macrophages. Similar results were obtained using the other test doses. Concentrations of IFN-γ were within 100 units/ml of elicited levels of $H_2O_2$ production by the macrophages which were significantly different than background values.

Calcitonin Inhibition of Macrophage Function

Figure 6:
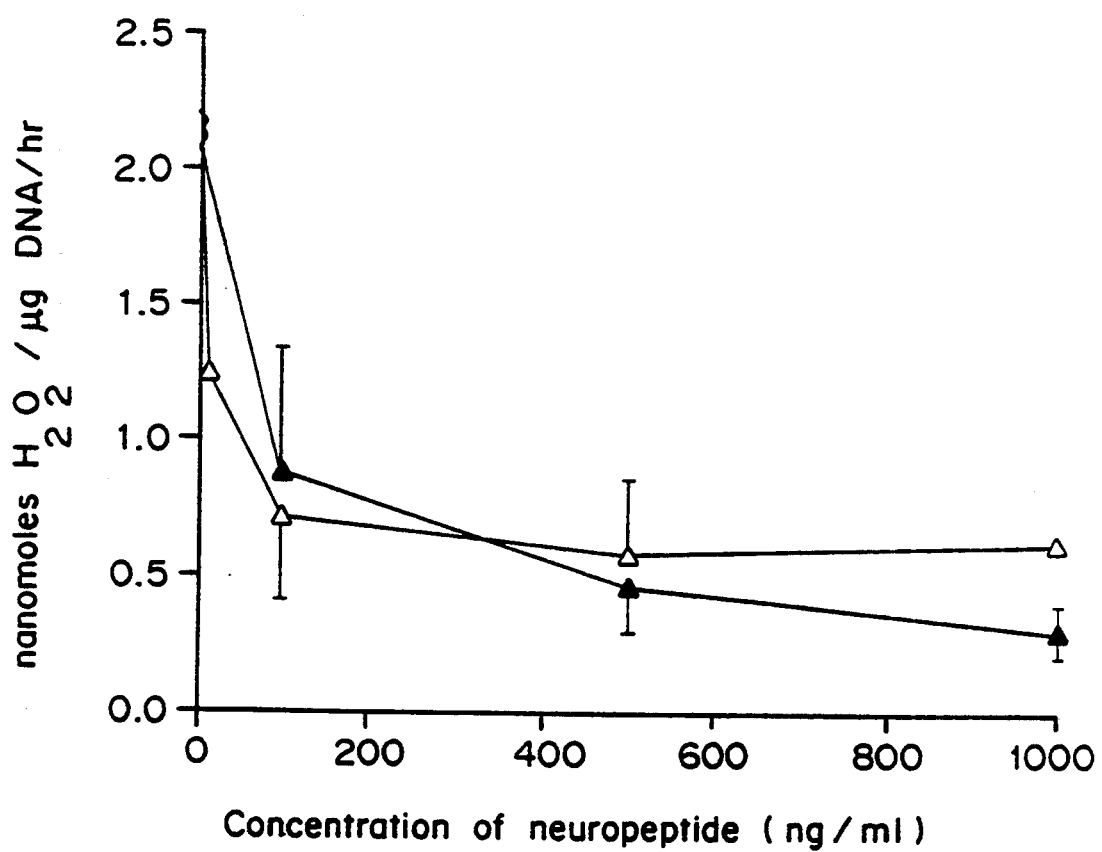
FIG. 6 is a graph comparing the effect of two neuropeptides, calcitonin ($\Delta$) and CGRP ($\Delta$) on macrophage function (vertical bars equal standard deviation).

Human macrophages were treated with the amounts of either CGRP (Δ) or calcitonin (Δ) indicated in FIG. 6, as a preincubation step for 3 hrs. The same procedure was followed as described above for CGRP. The cells were rinsed and IFN-γ (200 units/ml) was added. After 3 days incubation, $H_2O_2$ production was determined. The bars represent mean $H_2O_2$ production for triplicate cultures±SD. Since CGRP and calcitonin are nearly identical in molecular weight, 1000 ng/ml, a concentration of $2.5 \times 10^{-7}$ M, was used for the two substances. Calcitonin was found to inhibit $H_2O_2$ production by macrophages to a degree similar to that seen with CGRP (FIG. 6).

LP Inhibition Of Macrophage Function

Human macrophages were pretreated with varying doses of sand fly salivary gland lysates containing LP or medium for 3 hrs. The salivary material was washed away and the cells were activated with IFN-γ (200 units/ml). Three days later the amount of $H_2O_2$ produced by the cells in response to IFN-γ was determined as pM $H_2O_2$ per culture±SD. These data were normalized to the μg of DNA/culture to control for variation in cell numbers from culture to culture. The inhibition of the IFN-γ induced $H_2O_2$ response of the macrophages is shown in the Table below.

TABLE

| Pretreatment | Stimulation | Response {pM $H_2O_2$/μg DNA} |
|---|---|---|
| None | None | 20 ± 6 |
| Saliva {1 μg/ml} | None | 20 ± 0 |
| None | IFN-γ | 720 ± 190 |
| None | Saliva {1 μg/ml} + IFN-γ | 1170 ± 80* |
| Saliva {1 μg/ml} | IFN-γ | 80 ± 60 |
| None | Saliva {500 ng/ml} + IFN-γ | 960 ± 120* |
| Saliva {500 ng/ml} | IFN-γ | 190 ± 110 |

*No inhibition of the IFN-γ induced response since pretreatment with lysate required for inhibition.

CGRP Inhibition of Macrophage Presentation of Antigen

An OVA-specific T-cell line was produced in BALB/c mice (Titus et al., *S. Immunol.* 133:1594 (1984)). The line was L3T4+ and was maintained by successive cycles of restimulation and rest in vitro. (Kimono et al., *J. Exp. Med.* 152:759 (1980)). As a source antigen-presenting cells, BALB/c peritoneal cells (Titus et al., *Clin. Exp. Immunol.* 55:157, 1984) were placed into microtiter wells ($10^4$/well) in Dulbecco's modified Eagle's medium (DMEM) (Maryanski et al., *Eur. J. Immunol.* 12:401 (1982) supplemented with 5% fetal calf serum (Hyclone, Logan, Utah) and cultured overnight. Non-adherent cells were rinsed out of the wells, and medium with or without rat CGRP ($1.25 \times 10^{-7}$ M) was added as a pre-incubation step. Three hours later the wells were rinsed to remove the CGRP and the indicated number of OVA-specific T-cells (Sigma, St. Louis, Mo.) were added. At varying times thereafter, the wells were pulsed with 1 μCi$^3$H methylthymidine ($^3$H TdR) (Amersham, Arlington Heights, Ill.) and thymidine incorporation was assessed (Titus et al., *J. Immunol.* 133:1594 (1984)).

BALB/c peritoneal macrophages ($10^4$/well) were used as antigen-presenting cells. The macrophages were preincubated in $1.25 \times 10^{-7}$ M rat CGRP for three hrs., and the CGRP was then washed away. OVA-specific T-cells and OVA were then added to the cultures to assist the ability of the CGRP-treated macrophages to present antigen as measured by the degree of proliferation of the T-cells. Forty-eight hours later the cultures were pulsed with $^3$H TdR to assess the degree of proliferation of the T-cells. The numbers in the Table below represent the mean thymidine incorporation of quadruplicate cultures±SD. Background responses (macrophages+T-cells but no OVA, or T-cells+OVA but no macrophages) ranged between 300 to 500 CPM. Similar results were obtained with varying numbers ($10^3$ to $2 \times 10^4$/well) of peritoneal cell macrophages. The results in the Table indicate that the ability of murine macrophages to present OVA to an OVA-specific T-cell line was inhibited by CGRP. Similar results were obtained with different numbers of T-cells and different doses of OVA to stimulate the cultures. In addition, the inhibition of macrophage antigen presentation by CGRP was not due to simply delaying the kinetics of the response of the OVA-specific T-cells, since similar inhibition of proliferation of the T-cells was observed at day 2 of culture.

| Macrophages preincubated in | Number of T cells/ well | Response (CPM ± SD) to stimulation with | |
|---|---|---|---|
| | | 200 mg/ml OVA | 400 mg/ml OVA |
| Medium | 15,000 | 5,710 ± 1,300 | 8,450 ± 1,140 |
| CGRP | 15,000 | 1,620 ± 910 | 2,620 ± 700 |
| Medium | 30,000 | 5,230 ± 1,150 | 10,970 ± 800 |
| CGRP | 30,000 | 830 ± 500 | 3,380 ± 1,870 |

LP Inhibition of Macrophage Presentation of Antigen

The procedure followed was the same as that for CGRP. BALB/c peritoneal macrophages ($2 \times 10^4$/well) were preincubated with medium alone (positive control) or with the indicated concentrations of *L. longipalpis* salivary gland lysates containing LP for 3 hrs. and rinsed free of the material. $2 \times 10^4$ *Leishmania major* specific T cells and $2 \times 10^4$ *L. major* were then added to the cultures. Twenty-four hrs. later the cultures were pulsed with $^3$H to assess the degree of proliferation of the T cells. The numbers in the Table below represent the mean thymidine incorporation of triplicate cultures±SD.

| Macrophages preincubated in | Response {Mean $^3$H TdR incorporation} | % inhibition |
|---|---|---|
| Medium | 2065 ± 621 | N/A |

| Macrophages preincubated in | Response {Mean $^3$H TdR incorporation} | % inhibition |
| --- | --- | --- |
| 1 gland/ml | 726 ± 460 | 65 |
| 0.2 gland/ml | 1002 ± 901 | 51 |
| 0.05 gland/ml | 1882 ± 395 | 9 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An essentially pure protein obtained from the salivary gland lysate of the sand fly *Lutzomyia longipalpis* which protein induces vasodilation in a mammal and which is essentially free of all other lysate proteins.

2. A protein of claim 1, having a molecular weight of 6839 daltons as determined by mass spectrometry.

3. The protein of claim 1 having an elution profile in which it elutes before the calcitonin gene-related peptide (CGRP) elutes in an acetonitrile-H₂O-trifluoroacetic acid elution in a reverse-phase high-performance liquid chromatography column.

4. The protein of claim 1 having vasodilation activity as measured by erythema induction in mammal skin at least about 80–100 times that of CGRP.

5. A vasodilatory protein having the amino acid sequence shown in SEQ ID NO. 2.

6. A vasodilatory protein having the amino acid sequence shown in SEQ ID NO: 4.

7. A composition comprising a therapeutically effective amount a vasodilatory protein obtained from the salivary gland lysate of the sand fly *Lutzomyia longipalpis* and a pharmaceutically acceptable carrier.

8. A vasodilatory protein having the amino acid sequence of 18–80 as shown in SEQ ID NO: 4.

9. A method of increasing blood flow in the circulatory system of a mammal comprising parenterally administering to said mammal an amount of the protein of claim 1 effective to induce vasodilation.

10. A method of increasing blood flow locally in a vascular bed of a mammal comprising topically applying an amount of the protein of claim 1 to the vascular bed effective to induce vasodilation.

* * * * *